United States Patent [19]

Takenaka et al.

[11] 4,330,410
[45] May 18, 1982

[54] SEPARATION OF LEUKOCYTES FROM LEUKOCYTE-CONTAINING SUSPENSION BY FILTRATION

[75] Inventors: Yoshinori Takenaka; Nobuaki Tsuda; Toru Kuroda, all of Fuji, Japan

[73] Assignee: Asahi Kasei Kogyo Kabushiki Kaisha, Osaka, Japan

[21] Appl. No.: 170,384

[22] Filed: Jul. 21, 1980

Related U.S. Application Data

[63] Continuation of Ser. No. 16,478, Mar. 1, 1979, abandoned.

[30] Foreign Application Priority Data

Mar. 6, 1978 [JP] Japan ................................. 53/24454
Mar. 6, 1978 [JP] Japan ................................. 53/24455
Mar. 6, 1978 [JP] Japan ................................. 53/24458
Mar. 6, 1978 [JP] Japan ................................. 53/24476
Mar. 6, 1978 [JP] Japan ................................. 53/24477
Oct. 26, 1978 [JP] Japan ................................ 53/131010

[51] Int. Cl.$^3$ ............................................. B01D 37/00
[52] U.S. Cl. .................................... 210/767; 210/927
[58] Field of Search ............... 210/483, 491, 496, 505, 210/510, 600, 645, 927, 767; 422/44; 128/214 R

[56] References Cited

U.S. PATENT DOCUMENTS

3,593,854 7/1971 Swank ............................. 210/491 X
4,092,246 5/1978 Kummer ......................... 210/505 X Primary Examiner—Charles N. Hart
Assistant Examiner—David R. Sadowski
Attorney, Agent, or Firm—Sprung, Horn, Kramer & Woods

[57] ABSTRACT

Leukocytes are advantageously separated from blood or other leukocyte-containing suspensions by causing the leukocyte-containing suspensions to flow through a filter unit comprising a container provided with inlet and outlet conduit means and with a mass of fibers packed therein. The mass of fibers is characterized as possessing a bulk density of from 0.02 to 0.40 gram/cubic centimeter, and each of the fibers is characterized as having an average diameter of from 3 to 10 microns. The fibers to be used are selected from synthetic fibers, semi-synthetic fibers, regenerated fibers and natural proteinaceous fibers.

3 Claims, 5 Drawing Figures

SEPARATION OF LEUKOCYTES FROM LEUKOCYTE-CONTAINING SUSPENSION BY FILTRATION

This is a continuation of application Ser. No. 16,478, filed Mar. 1, 1979, abandoned.

BACKGROUND OF THE INVENTION

This invention relates to a method for separating leukocytes from a leukocyte-containing suspension by filtration, and to a filter unit used therefor.

By the term "leukocyte-containing suspension" used herein is meant blood, ascites, bone marrow and other leukocyte- or leukocyte precursor cell-containing body fluids. This term should also be interpreted as including physically, chemically and/or biologically treated blood and other body fluids such as, for example, blood diluted with a physiological solution, erythrocyte agglutinant-(such as dextran or hydroxyethyl-starch)- incorporated blood, a buffy coat and other leukocyte-containing suspension layers prepared by centrifugation or cell-electrophoresis.

In recent years component transfusions have often been employed in place of whole blood transfusions. Component transfusions involve transfusing the particular blood components needed or desired for the patients, and are advantageous in that the needed components, separated from unneeded or injurious components, are administered in a desirably high concentration. Particularly, a leukocyte or granulocyte transfusion for infected leukopenic patients and a leukocyte-poor, erythrocyte-rich blood transfusion for preventing graft versus host (GVH) reaction from occurring due to imcompatibility of histocompatibility antigens are now in frequent use.

It is also a popular practice to prepare leukocyte or erythrocyte suspensions of a high purity for the purpose of studying blood cells.

Various processes have been employed for carrying out leukocyte separation. Typical separation processes include, for example, an agglutinant incorporation-sedimentation process, a centrifugation process and a filtration process utilizing a filter composed of a leukocyte-adherent material. The agglutinant incorporation-sedimentation process involves incorporating an erythrocyte agglutinant such as dextran or hydroxyethyl-starch into a leukocyte-containing suspension, and then subjecting the agglutinant incorporated liquid to sedimentation to separate the liquid into an erythrocyte sediment and a leukocyte-containing liquid layer. This process has several disadvantages in that it requires a substantial period of time for the separation to be completed, in that the resulting leukocyte suspension is of a low purity, and in that it is often required to remove the agglutinant from the resulting leukocyte suspension. The centrifugation process involves, for example, placing a plurality of liquids of different densities, one upon another, in a vessel to form density gradient superposed layers; placing blood on the top liquid layer; and then centrifuging the superposed layers thereby to separate the blood into several layers. This centrifugation process is not suitable for the separation of a large amount of blood. The filtration process involves passing blood through a filter composed of a leukocyte-adherent material such as polyamide fibers, polyester fibers, siliconized glass wool and absorbent cotton thereby to entrap granulocytes and monocytes in the filter, and then passing a physiological solution through the filter to collect the entrapped leukocyte components. This filtration process is not suitable for the separation of lymphocytes, particularly for collecting a lymphocyte-rich suspension of a high purity.

SUMMARY OF THE INVENTION

It is the main object of the present invention to provide a filter unit for separating leukocytes including lymphocytes from a leukocyte-containing suspension, which filter unit insures an effective filtration of the leukocyte-containing suspension and an effective collection of leukocyte components with enhanced yield and purity.

Other objects and advantages of the present invention will become apparent from the following description.

In accordance with the present invention there is provided a filter unit for separating leukocytes from a leukocyte-containing suspension, comprising a container provided with at least one inlet conduit means and at least one outlet conduit means, the container having packed therein a mass of fibers which have no deleterious effects on leukocytes and other blood components and which possess an average fiber diameter of from 3 to 10 microns, the mass of fibers having a bulk density of from 0.02 to 0.40 gram/cubic centimeter, and the fibers being of at least one type of fibers selected from the group consisting of synthetic fibers, semi-synthetic fibers, regenerated fibers and natural proteinaceous fibers.

BRIEF DESCRIPTION OF THE DRAWINGS

The accompanying drawings illustrate the criticality of the fiber diameter and the criticality of the bulk density of the mass of fibers contained in the filter unit. In the drawings.

DESCRIPTION OF THE PREFERRED EMBODIMENTS

The fibers to be packed in the container of the filter unit are selected from synthetic fibers, semi-synthetic fibers, regenerated fibers and natural proteinaceous fibers. One of these mentioned types of fibers may be used by itself or a combination of the different types mentioned may be used. The fibers used should not have any deleterious effects on leukocytes and other blood components. Accordingly, the fibers should not be made of polymers which have moieties exhibiting, for example, a hemolytic function, and should not be treated with oiling agents which are harmful to blood. Preferable fibers may be selected from synthetic fibers such as acrylonitrile polymer (homopolymer and copolymer) fibers, polyamide fibers and polyester fibers, semi-synthetic fibers such as cellulose acetate fibers, and natural proteinaceous fibers such as silk.

The term "fiber diameter" used herein is defined by the following equation:

$$D = 2\sqrt{\frac{x}{\pi \cdot p \cdot y}}$$

where D is the diameter of the fiber in centimeters, x is the weight of the fiber in grams, y is the length of the fiber in centimeters, and p is the density of the fiber in gram/cubic centimeter. The fibers used are generally of a circular cross-section, but the above-mentioned definition for the fiber diameter should also be applied to fibers of a non-circular cross-section.

The container in which the mass of fibers is to be packed may be of any shape provided that the container has at least one inlet conduit and at least one outlet conduit through which a leukocyte-containing suspension and other treated body fluids or physiological solutions can be introduced into and withdrawn from the container, respectively. It is convenient, however, that the container be of a columnar shape, i.e., a cylindrical shape or a circular truncated cone shape, in view of ease in operation. It is also convenient that the container be provided, at locations upstream to and downstream from the mass of fibers, with mesh screens or other similar filters in order to prevent the fibers from escaping out of the container. The container may be made of a non-deleterious material such as glass, polyethylene, polypropylene, polystyrene and polyvinyl chloride.

By the term "bulk density" used herein is meant a numerical value expressed in grams/cubic centimeter obtained by dividing the weight (in grams) of the mass of fibers by the volume of the mass of fibers, i.e., the inner volume of the container when the container is completely filled with the mass of fibers.

The mass of fibers packed in the container should preferably have identical bulk densities in any portion of the mass of fibers. It is preferable that the fibers be unbound into single fibers before being packed into the containers. The fibers should also preferably possess a particular length by which the fibers can be kept together in the form of an entangled or interlaced mass. If the fibers are too short, they will tend to escape from the container together with the liquid flowing through the container. For this reason the fibers should preferably possess a length which is at least approximately equal to that of commercially available fibers popularly employed in the textile industry. In particular, fibers of at least 30 centimeters in length cut from continuous filaments are most preferable for use in this case.

The amount of the fibers to be packed is mainly determined by the particular leukocyte-containing liquid to be treated and the flow rate thereof. Fibers of different materials and/or of different diameters may be used in combination provided that the average diameter is not greater than 10 microns. Furthermore, a minor amount of fibers having average diameters which are greater than 10 microns may be incorporated into the mass of fibers to maintain the mass of fibers at a constant bulk density during operation. The mass of fibers should preferably be in the form of a mass of entangled or interlaced fibers, but such mass may be in a woven, non-woven or knitted fabric form.

Figure 1:
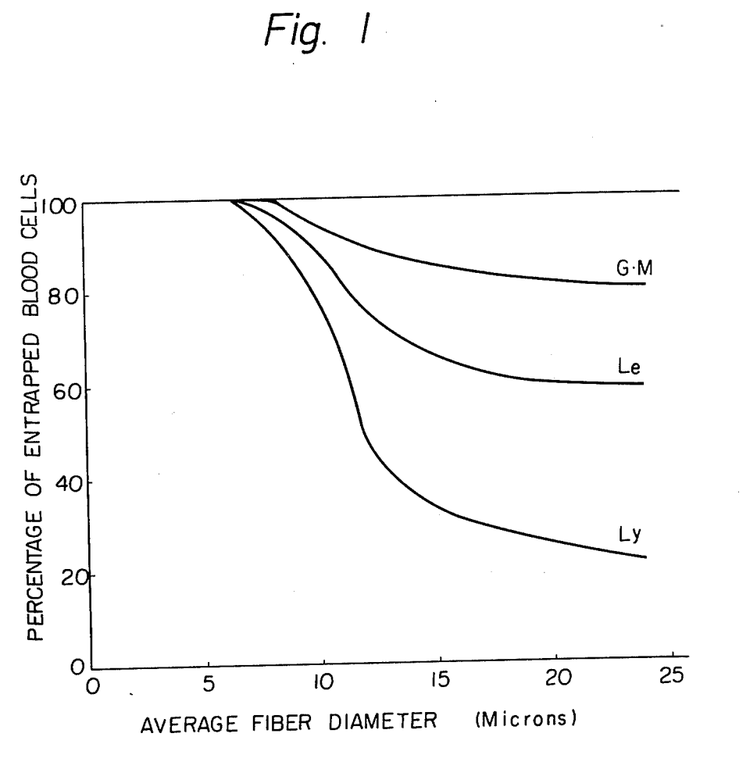
FIG. 1 is a graph showing the dependency of the percentage of entrapped blood cells upon the average fiber diameter as determined at a fiber bulk density of 0.085 gram/cubic centimeter.
Figure 2:
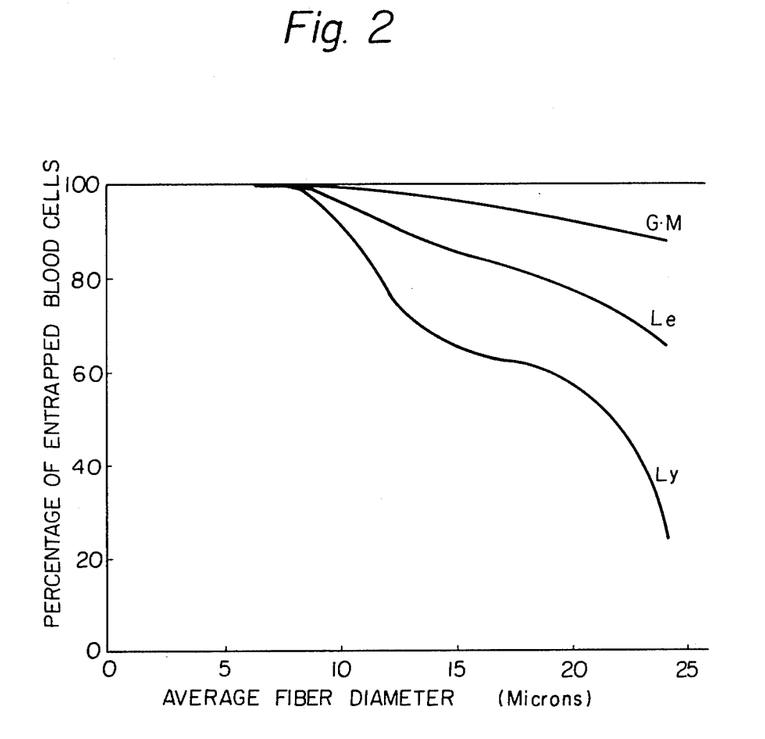
FIGS. 2 and 3 are graphs showing the dependency of the percentage of entrapped blood cells upon the average fiber diameter as determined at a fiber bulk density of 0.15 gram/cubic centimeter.
Figure 3:
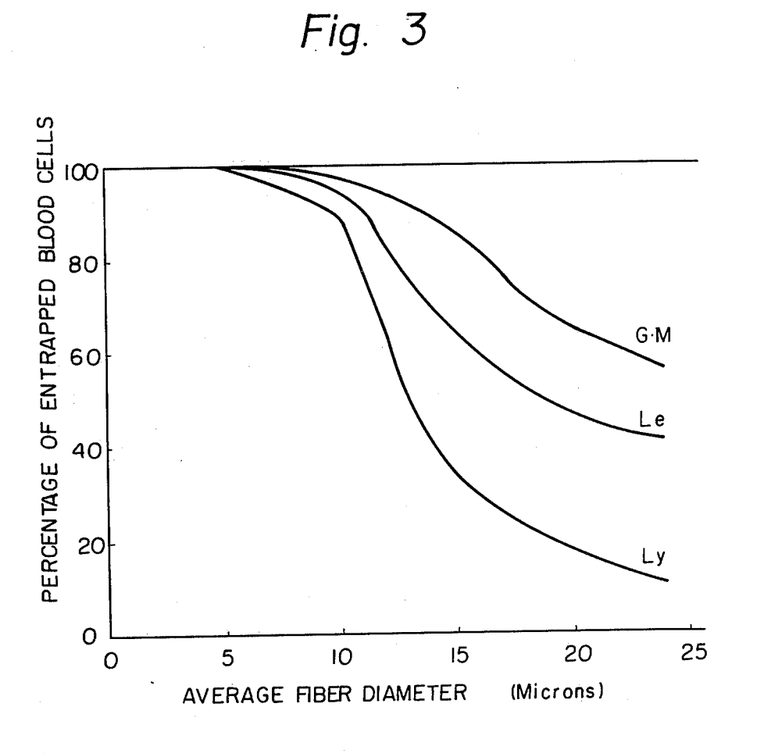

Referring now to FIGS. 1, 2 and 3 which show the dependency of the percentage of leukocyte components trapped by the filter upon the average diameter of the fibers in the filter. In FIGS. 1, 2 and 3, curves Le, G.M and Ly refer to the percentages of leukocytes, granulocytes plus monocytes, and lymphocytes, respectively, entrapped by the filter.

The percentages of the respective leukocyte components are defined by the following equation:

% of entrapped leukocyte component $= (B/A) \times 100$ where A is the number of the cells of each leukocyte component in the original (i.e., untreated) leukocyte-containing suspension, and B is the number of the cells of each leukocyte component entrapped by the filter.

The curves Le, G.M and Ly in FIGS. 1 and 2 were obtained as follows. Polyacrylonitrile fibers having various average diameters were separately packed into a cylindrical polyvinyl chloride column at bulk densities of 0.085 gram/cubic centimeter (in FIG. 1) and 0.15 gram/cubic centimeter (in FIG. 2). The cylindrical polyvinyl chloride column exhibited an inner diameter of 1.0 centimeter and a length of 10 centimeters. Twenty milliliters of blood were pumped into the polyacrylonitrile fiber-packed column. The blood flowed through the column at a flow rate of 2 milliliters/minute. During the flowing period, leukocyte components were entrapped by the mass of polyacrylonitrile fibers. Then, 30 milliliters of a physiological sodium chloride solution were pumped to flow through the column at a flow rate of 5 milliliters/minute. When at least 99% of the erythrocytes contained in the original blood had been recovered, the numbers of the cells of the respective leukocyte components not entrapped by the mass of fibers and still present in the liquid passed through the column were measured. The numbers (B) of the cells of the respective leukocyte components entrapped by the mass of fibers were obtained by subtracting the above-mentioned numbers of the unentrapped cells from the numbers (A) of the cells of the respective leukocyte components present in the original blood, and the percentages of the entrapped leukocyte components were thereafter calculated from A and B. The blood used was heparinized blood of a temperature of 23° C. containing $5.0 \times 10^6$ erythrocytes/microliter, $2.5 \times 10^5$ platelets/microliter and 6,600 leukocytes/microliter (2,300 lymphocytes/microliter and 4,300 granulocytes plus monocytes/microliter). The above-mentioned experiment was carried out at a temperature of 25° C.

As is apparent from FIGS. 1 and 2, a large amount of granulocytes and monocytes can still be entrapped even when the average diameter of the fibers is greater than 20 microns. In contrast, a significant amount of lymphocytes can be entrapped only when the average diameter of the fibers is small, i.e., below approximately 10 microns. In general, the smaller the average diameter of the fibers, the larger the percentage of entrapped leukocyte components. Furthermore, the percentage of entrapped leukocyte components obtained at a fiber bulk density of 0.15 gram/cubic centimeter is larger than the percentage of entrapped leukocyte components obtained at a fiber bulk density of 0.085 gram/cubic centimeter. One of the reasons why fibers having an average diameter of not greater than 10 microns are advantageous is presumed as follows. When blood or another leukocyte-containing suspension is continued to be flowed through the fiber-packed column, the inner pressure of the column undesirably increases. Such pressure increase is closely related to the bulk density of the packed fibers, that is, the smaller the bulk density, the smaller the pressure increase. Fibers having an average diameter of not greater than 10 microns have a good capability for entrapping leukocyte components when the bulk density of such fibers is small.

If the average diameter of the fibers is less than 3 microns, it then becomes difficult to maintain the bulk density of the packed fibers within the desired density range. Thus, the fibers to be used should have an average diameter of from 3 to 10 microns.

When the bulk density of the packed fibers exceeds 0.40 gram/cubic centimeter, it then becomes difficult to pump blood or other leukocyte-containing suspension through the fiber-packed column. In contrast, when the bulk density is less than 0.02 gram/cubic centimeter, the packed fibers cannot entrap leukocyte components effectively.

Referring to FIG. 3, curves Le, G.M and Ly were obtained in a manner similar to that mentioned with reference to FIG. 2 except that the blood flow rate was changed to 4 milliliters/minute.

As shown by a comparison of the curves in FIG. 3 with those in FIG. 2, as the blood flow rate is increased, the percentages of the entrapped lymphocytes and granulocytes plus monocytes will decrease when the average fiber diameter is greater than 10 microns, and increase when the average fiber diameter is 10 microns or less.

When blood or other leukocyte-containing suspensions are caused to flow through the filter unit of the present invention by using a pump, the leukocyte components are selectively entrapped by the mass of fibers of the filter unit. The entrapped leukocyte components are not readily detached from the mass of fibers when a washing liquor such as a physiological sodium chloride solution is caused to flow therethrough in order to wash out the erythrocytes, platelets and plasma remaining in the mass of fibers.

It is also possible to cause blood or other leukocyte-containing suspensions to flow through the filter unit by an instillation procedure, i.e., procedure causing blood, etc., to enter into the filter unit drop by drop by means of gravity, instead of by using a pump. In this case, it is preferable that the mass of fibers has a bulk density of from 0.04 to 0.15 gram/cubic centimeter and an average fiber diameter of from 5 to 10 microns. The fiber unit containing such mass of fibers is suitable (particularly when the volume of the mass of fibers is from 25 to 60 milliliters) for causing 200 to 500 milliliters of a leukocyte-containing suspension to flow therethrough at a flow rate of from 5 to 10 milliliters/minute.

When the average diameter of the fibers in the above-mentioned filter unit used to carry out an instillation procedure is less than 5 microns, it is difficult to maintain the bulk density of the packed fibers at a desired range during the entire period of treating a leukocyte-containing suspension. Furthermore, when the bulk density is less than 0.04 gram/cubic centimeter, the filter unit does not exhibit a good capability for entrapping leukocyte components. In contrast, when the bulk density exceeds 0.15 gram/cubic centimeter, it becomes difficult to maintain the flow rate between 5 and 10 milliliters/minute if instillation is employed.

The filter unit of the present invention is useful for removing lymphocytes and other leucocyte components from a leukocyte-containing suspension, e.g., heparinized blood, ACD solution-incorporated blood and an erythrocyte rich suspension (Packed Red Cell, PRC) prepared from ACD solution-incorporated blood. It is expected that a GVH reaction, which tends to occur due to incompatibility of histocompatibility antigens particularly when a whole blood transfusion is carried out in a large quantity, can be prevented or minimized by using the blood treated by the filter unit of the present invention.

Furthermore, by using the filter unit of the present invention, it is also possible to collect the leukocyte components in the thus-filtered suspension with a high degree of purity. For this purpose, it is preferable that the filter unit contains a mass of packed fibers which has a bulk density of from 0.04 to 0.25 gram/cubic centimeter and an average fiber diameter of from 7 to 10 microns.

Figure 4:
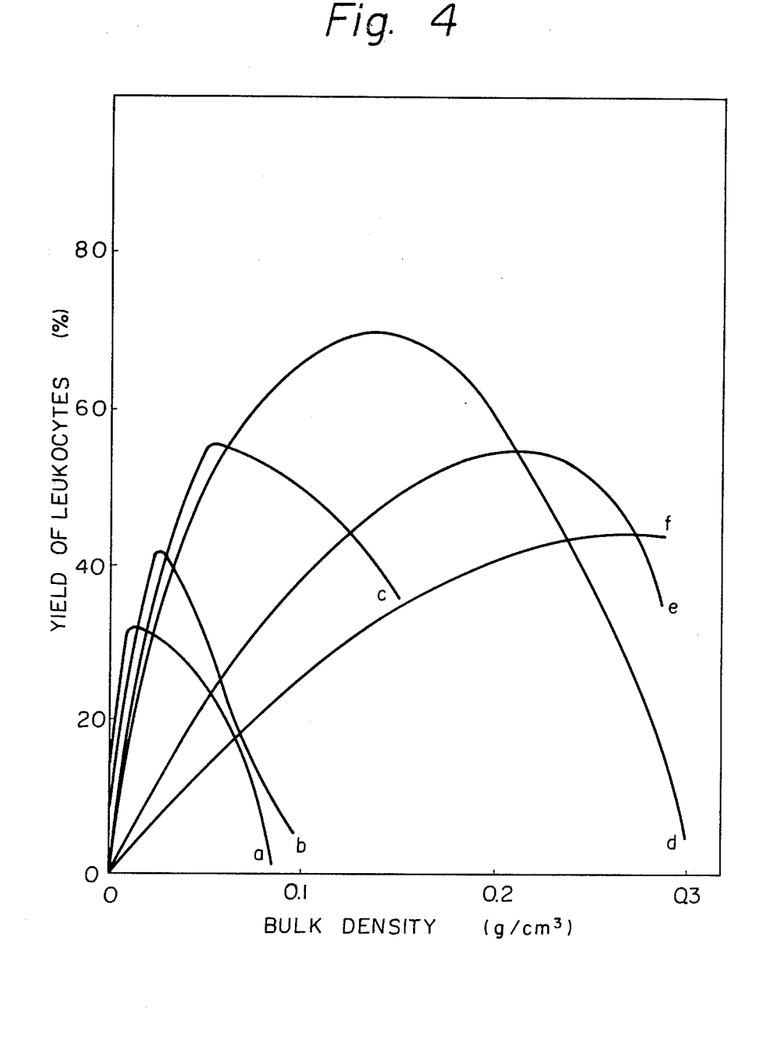
FIG. 4 is a graph showing the dependency of the percentage yield of leukocytes upon the bulk density of the mass of fibers; and, FIG. 5 is a graph showing the dependency of the percentage yield of lymphocytes upon the bulk density of the mass of fibers.
Figure 5:
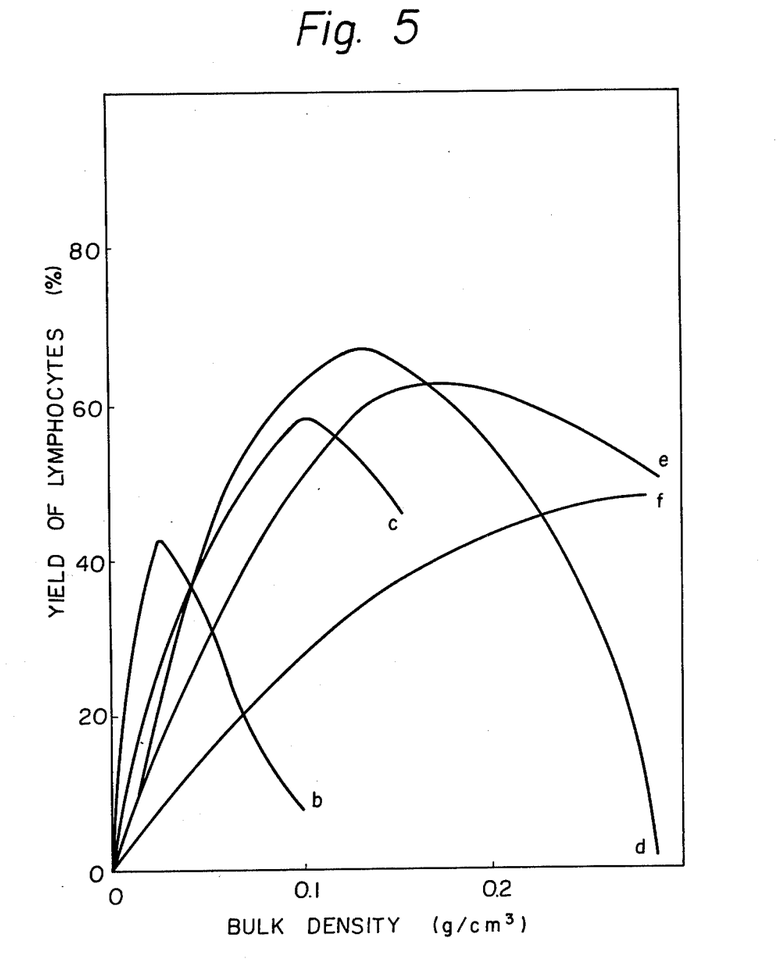

The criticality of the bulk density and the average fiber diameter of the packed fibers in the filter unit suitable for entrapping leukocytes therein and for collecting the entrapped leukocytes will be explained with reference to FIGS. 4 and 5. FIG. 4 shows the relationships between the percentage yield of leukocytes and the fiber bulk density, and between such yield and the average fiber diameter; FIG. 5 shows the relationships between the percentage yield of lymphocytes and the fiber bulk density, and between such yields and the average fiber diameter. The term "percentage yield of leukocytes or lymphocytes" used herein refers to that defined by the following equation:

$$\% \text{ Yield} = (B/A) \times 100$$

where A is the number of leukocytes or lymphocytes in the original, i.e., untreated, leukocyte-containing suspension, and B is the number of collected leukocytes or lymphocytes.

The curves a through of in FIGS. 4 and 5 were obtained from the results of the following experiments. Polyacrylonitrile fibers having various average diameters were separately packed at various bulk densities into a cylindrical polyvinyl chloride column having an inner diameter of 1.8 centimeters and a length of 10 centimeters. One hundred milliliters of blood were caused to flow through the fiber-packed column at a flow rate of 10 milliliters/minute whereby leukocyte components were entrapped in the column, and then 150 milliliters of a physiological sodium chloride solution were caused to flow therethrough at a flow rate of 10 milliliters/minute. Finally, 100 milliliters of a phosphate-buffered saline containing 17.5 milligrams/milliliter of serum albumin were caused to flow through the column at a flow rate of 10 milliliters/minute, while the periphery of the column was tapped by a wooden stick at a rate of 100 times/minute, whereby the entrapped leukocyte components were collected from the column. The blood used was heparinized blood maintained at a temperature of 25° C. and containing $4.8 \times 10^6$ erythrocytes/microliter, 6500 leukocytes/microliter (2300 lymphocytes/microliter and 4200 granulocytes plus monocytes/microliter) and $2.1 \times 10^5$ platelets/microliter. The experiments were carried out at a temperature of 25° C. The curves a, b, c, d, e and f correspond to the average fiber diameters of 5.2, 6.2, 7.4, 8.5, 10.0 and 16.0 microns, respectively.

FIG. 4 shows that the yield of leukocytes is at least approximately 50% when the bulk density of the packed fibers is in the range of from 0.04 to 0.25 gram/cubic centimeter and the average fiber diameter is in the range of from 7 to 10 microns. FIG. 5 shows that the yield of lymphocytes is satisfactory when the bulk density of the packed fibers and the average fiber diameter are in the above-mentioned ranges. From the standpoint of percentage yield of lymphocytes, it is preferable that the bulk density and the average fiber diameter be in the ranges of from 0.06 to 0.20 gram/cubic centimeter and from 8.0 to 9.5 microns, respectively.

The collection of the leukocyte components entrapped in the filter unit may be effected by causing a physiological solution to flow through the filter unit while the flow rate is maintained at a high level, or while the mass of fibers is vibrated or while an external physical force is imparted to the filter unit so that gaps between the fibers are enlarged. One preferable method involves flowing a physiological solution through the filter unit while the container of the filter unit is tapped by a wooden stick. A material for enhancing detachment of the leukocytes entrapped in the filter unit, such as acid-citrate-dextrose (ACD) and ethylenediaminetetraacetate, may be incorporated into the physiological solution.

When blood is flowed through the filter unit, a substantial portion of leukocytes and a still large amount of erythrocytes, platelets and plasma remain in the filter unit. It is, therefore, preferably that erythrocytes, platelets and plasma remaining in the filter unit be washed out from the filter unit prior to collecting leukocytes therefrom. The process of washing out the filter unit may be effected by flowing a physiological solution such as a physiological sodium chloride solution and a phosphate-buffered saline through the filter unit. The suspension of leukocytes collected after washing out of the filter unit contains only an extremely minor amount of erythrocytes and other components. It has been found that the amount of erythrocytes and other components present in the collected leukocyte suspension generally corresponds to the bulk density of the packed fibers, that is, the smaller the bulk density, the smaller the amount of erythrocytes and other components.

Before blood or other leukocyte-containing suspensions are caused to flow through the filter unit, plasma components such as plasma, serum and serum albumin may be flowed through the filter unit first. By this initial introduction of plasma components, the amount of erythrocytes and other components present in the final suspension of leukocytes collected from the filter unit can be reduced by a very great extent.

The blood cell suspensions treated by using the filter unit of the present invention have satisfactory properties. That is, when blood is caused to flow by means of a pump through the filter unit having a fiber bulk density of from 0.02 to 0.40 gram/cubic centimeter and an average fiber diameter of from 3 to 10 microns or caused to flow by means of instillation through the filter unit having a bulk density of from 0.04 to 0.15 gram/cubic centimeter and an average fiber diameter of from 5 to 10 microns, the erythrocytes contained in the resulting erythrocyterich suspensions exhibit little or no morphological or biochemical change. When blood is caused to flow through the filter unit having a fiber bulk density of from 0.04 to 0.25 gram/cubic centimeter and an average fiber diameter of from 7 to 10 microns and then the entrapped leukocytes are collected from the filter unit, the resulting granulocytes and monocytes exhibit good motility and phagocytic ability, and the resulting lymphocytes can be blastotransformed by various mitogens such as phytohemagglutinin and pokeweed mitogen to an extent similar to that of lymphocytes prepared by other methods. Furthermore, the proportion of T-cells to B-cells is approximately the same as that of the original blood.

By using the filter unit of the present invention, leukocytes can be removed or collected in a simple operation and within a short period of time. Thus, such filter unit can enable erythrocyte or leukocyte component transfusion to be easily conducted in medical facilities. It will also be easy to fractionate or adopt a minor amount of erythrocytes or leukocytes required for various medical tests or researches.

The invention will be further illustrated by the following examples carried out at room temperature, in which examples, percentages are shown by numbers of blood cells.

EXAMPLE 1

2.7 grams of polyacrylonitrile fibers having an average diameter of 5.2 microns and a length of from 4 to 7 centimeters were uniformly packed at a bulk density of 0.086 gram/cubic centimeter into a cylindrical polypropylene column having a diameter of 2 centimeters and a length of 10 centimeters, thereby to prepare a leukocyte separation filter. One hundred milliliters of heparinized blood from a healthy human donor were pumped through the polyacrylonitrile fiber-packed column at a flow rate of 5 milliliters/minute, and then 30 milliliters of a physiological sodium chloride solution were flowed therethrough at a flow rate of 5 milliliters/minute to recover erythrocytes remaining in the column, whereby approximately 100 milliliters of a leukocyte-poor blood were obtained. The leukocyte-poor blood contained 3% of the original leukocytes (8% of the original lymphocytes) and 93% of the original erythrocytes, i.e., based on the respective numbers of the corresponding components in the original blood. The resultant blood contained neither granulocytes nor monocytes.

EXAMPLE 2

5.7 grams of polyacrylonitrile fibers having an average diameter of 8.2 microns and a length of from 6 to 8 centimeters were uniformly packed at a bulk density of 0.095 gram/cubic centimeter into a cylindrical polystyrene column having a diameter of 3.15 centimeters and a length of 7.7 centimeters, thereby to prepare a leukocyte separation filter. Two hundred milliliters of heparinized blood from a healthy human donor were caused to flow drop by drop through the polyacrylonitrile fiber-packed column at a flow rate of 6.67 milliliters/minute, and thereafter 55 milliliters of a physiological sodium chloride solution were similarly flowed therethrough to recover erythrocytes remaining in the column, whereby approximately 200 milliliters of leukocyte-poor blood were obtained. The leukocyte-poor blood contained 6% of the original leukocytes (3% of the original granulocytes plus monocytes and 11% of the original lymphocytes) and 97% of the original erythrocytes, i.e., based on the respective numbers of the corresponding components in the original blood.

EXAMPLE 3

3.621 grams of polyester fibers having an average diameter of 7.8 microns and a length of from 4 to 7 centimeters were uniformly packed at a bulk density of 0.12 gram/cubic centimeter into a cylindrical polystyrene column having a diameter of 2.8 centimeters and a length of 4.9 centimeters, thereby to prepare a leukocyte separation filter. Two hundred and thirty milliliters of ACD-incorporated fresh blood from a healthy human donor were centrifuged, followed by separating 100 milliliters of plasma from the blood to obtain 130 milliliters of an erythrocyte-rich blood. Seventy milliliters of a physiological sodium chloride solution were added to the so-obtained erythrocyte-rich blood to obtain 200 milliliters of a blood cell liquid. The blood cell liquid was caused to flow drop by drop through the polyester fiber-packed column at a flow rate of 8 milliliters/minute, and then 28 milliliters of a physiological sodium chloride solution were similarly flowed therethrough to recover erythrocytes remaining in the column, whereby approximately 200 milliliters of a leukocyte-poor erythrocyte-rich liquid were obtained. This liquid contained 10% of the original leukocytes (9% of the original granulocytes plus monocytes and 12% of the original lymphocytes) and 94% of the original erythrocytes.

EXAMPLE 4

Polyacrylonitrile fibers having an average diameter of 8.2 microns and a length of from 4 to 7 centimeters were well unbound into single fibers, and then 3.817 grams of the fibers were uniformly packed at a bulk density of 0.150 gram/cubic centimeter into a cylindrical polyvinyl chloride column having an inner diameter of 1.8 centimeters and a length of 10 centimeters, thereby to prepare a leukocyte separation filter. One hundred milliliters of heparinized blood from a healthy human donor were flowed through the polyacrylonitrile fiber-packed column at a flow rate of 10 milliliters/minute, and thereafter 150 milliliters of a physiological sodium chooride solution were flowed therethrough at a flow rate of 10 milliliters/minute to wash out substantial portions of the erythrocytes, platelets and plasma remaining in the column. Thereafter, a physiological sodium chloride solution of 6.5 pH, having incorporated therein 17.5 milligrams/milliliter of human serum albumin and 12.5% of an ACD solution was flowed through the column at a flow rate of 10 milliliters/minute while the periphery of the column was tapped with a wooden stick at a rate of 100 times/minute, thereby to collect leukocytes. The liquid so obtained contained 67% of the original leucocytes (68% of the original lymphocytes and 66% of the original granulocytes plus monocytes). The obtained liquid contained only negligible amounts of erythrocytes and platelets.

EXAMPLE 5

4.71 grams of various fibers, shown in Table I, below, having an average diameter of from approximately 9 to 10 microns were separately packed uniformly at a bulk density of 0.15 gram/cubic centimeter into cylindrical polyvinyl chloride columns each having an inner diameter of 2 centimeters and a length of 10 centimeters, thereby to prepare leukocyte separation filters. Two hundred milliliters of heparined blood were flowed through each of the fiber-packed columns at a flow rate of 10 milliliters/minute; then 180 milliliters of a physiological sodium chloride solution were flowed through the columns at a flow rate of 10 milliliters/minute. Finally, 100 milliliters of a phosphate-buffered saline having incorporated therein 17.5 milligrams/milliliter of serum albumin were flowed through each column at a flow rate of 10 milliliters/minute over a period of 10 minutes while the periphery of the column was tapped with a wooden stick at a rate of 100 times/minute. The liquid withdrawn from the column contained leukocytes (lymphocytes, granulocytes and monocytes) in amounts shown in Table I, below, based on the respective numbers of the corresponding components contained in the original heparinized blood.

TABLE I

| Fibers | Average diameter (microns) | Bulk density (g/cm³) | Yield of leukocytes (%) | Yield of lymphocytes (%) | Yield of granulocytes + monocytes (%) |
|---|---|---|---|---|---|
| Cellulose diacetate fibers | 9.9 | 0.150 | 55.6 | 55.0 | 55.9 |
| Polyacrylonitrile fibers | 9.2 | 0.150 | 64.2 | 65.0 | 63.8 |
| Polycapramide fibers | 9.8 | 0.150 | 58.3 | 55.3 | 59.9 |
| Polyethylene terephthalate fibers | 9.6 | 0.150 | 55.0 | 53.1 | 56.0 |

As is apparent from Table I, there are no great differences among the yield percentages of the respective collected leukocyte components with respect to the various fibers packed in the column, in the case where the fiber diameter is approximately 9 to 10 microns.

EXAMPLE 6

Polyacrylonitrile fibers having an average diameter of 8.2 microns and a length of from 4 to 7 centimeters were well unbound into single fibers, and then 0.517 gram of the fibers was uniformly packed at a bulk density of 0.132 gram/cubic centimeter into a cylindrical polyvinyl chloride column having an inner diameter of 1 centimeter and a length of 5 centimeters thereby to prepare a leukocyte separation filter. Five milliliters of heparinized blood from a healthy human donor were flowed through the polyacrylonitrile fiber-packed column over a period of one minute, and then 20 milliliters of a physiological sodium chloride solution were flowed therethrough at a flow rate of 5 milliliters/minute to wash out substantial portions of the erythrocytes, platelets and plasma remaining in the column. Thereafter, 4 milliliters of a physiological sodium chloride solution were forced into the column within a short period of time, by using an injector, through the intake conduit located opposite to the conduit through which the heparinized blood and the washing physiological sodium chloride solution entered, thereby to collect leukocytes. The so-obtained liquid contained 72% of the original leukocytes (66% of the original lymphocytes and 75% of the original granulocytes plus monocytes).

EXAMPLE 7

Polyester fibers having an average diameter of 7.8 microns and a length of from 4 to 7 centimeters were well unbound into single fibers, and then, 4.58 grams of the fibers were uniformly packed at a bulk density of 0.18 gram/cubic centimeter into a cylindrical polyvinyl chloride column having an inner diameter of 1.8 centimeters and a length of 10 centimeters, thereby to prepare a leukocyte separation filter. One hundred milliliters of heparinized blood from a healthy human donor were flowed through the polyester fiber-packed column at a flow rate of 5 milliliters/minute, and then 150 milliliters of a physiological sodium chloride solution were flowed therethrough at a flow rate of 5 milliliters/minute to wash out substantial portions of the erythrocytes, platelets and plasma remaining in the column. Thereafter, 100 milliliters of a phosphate-buffered saline having a pH of 7.4 were forced into the column for 20 seconds, by using an injector, through the intake conduit located opposite to the conduit through which the heparinized blood and the washing physiological sodium chloride solution were introduced, thereby to collect leukocytes. The so obtained liquid contained 63% of the original leukocytes (64% of the original lymphocytes and 62% of the original granulocytes plus monocytes).

EXAMPLE 8

A bundle of 200 polyester continuous filaments each having an average diameter of 9.1 microns was, after the filament bundle was unbound, cut into fibers having a length of 103.5 centimeters. The fibers were packed at a bulk density of 0.15 gram/cubic centimeter into a cylindrical polyvinyl chloride column having an inner diameter of 1 centimeter and a length of 2.5 centimeters, thereby to prepare a leukocyte separation filter. Five milliliters of heparinized blood from a healthy human donor were flowed through the polyester fiber-packed column at a flow rate of 3 milliliters/minute, and then 20 milliliters of a phosphate-buffered saline were flowed therethrough at a flow rate of 4 milliliters/minute to wash out substantial portions of the erythrocytes, platelets and plasma remaining in the column. Thereafter, 4 milliliters of a physiological sodium chloride solution were forced into the column within a short period of time, by using an injector, through the intake conduit located opposite to the conduit through which the heparinized blood and the washing physiological sodium chloride solution were introduced, thereby to collect leukocytes from the column. The so-obtained liquid contained 63% of the original leukocytes (65% of the original lymphocytes and 62% of the original granulocytes plus monocytes). These results showed that there were no great differences between a short-staple fiber filter and a long stable fiber filter in their capabilities to separate and collect the respective leukocyte components.

What we claim is:

1. A method for separating unaltered and unaggregated leukocytes from an unaltered and unaggregated leukocyte-containing suspension, comprising the step of passing said leukocyte-containing suspension through a container provide with at least one inlet conduit means and with at least one outlet conduit means, said container having packed therein a mass of fibers which have no deleterious effects on leukocytes and other blood components and which possess an average fiber diameter of from 3 to 10 microns, said mass of fibers having a bulk density of from 0.02 to 0.40 gram/cubic centimeter, and said fibers being of at least one type of fibers selected from the group consisting of cellulose acetate fibers, acrylonitrile polymer fibers, polyamide fibers and polyester fibers; whereby a substantial part of the unaltered and unaggregated leukocytes is entrapped in said mass of fibers and a leukocyte-poor liquid is obtained.

2. A method according to claim 1 wherein said leukocyte-containing suspension is caused to flow, by means of instillation, through the container having packed therein said mass of fibers having a bulk density of from 0.04 to 0.15 gram/cubic centimeter and an average fiber diameter of from 5 to 10 microns, whereby a substantial part of the leukocytes is entrapped in said mass of fibers and a leukocyte-poor liquid is obtained.

3. A method according to claim 1 wherein said leukocyte-containing liquid is passed through said container having packed therein said mass of fibers having a bulk density of from 0.04 to 0.25 gram/cubic centimeter and an average fiber diameter of from 7 to 10 microns, thereby to entrap a substantial part of leukocytes in said mass of fibers; and then said entrapped leukocytes are collected from said fiber mass-packed container.

* * * * *